United States Patent [19]

Berger

[11] Patent Number: 4,571,181

[45] Date of Patent: Feb. 18, 1986

[54] DENTAL THICKNESS GAUGE

[76] Inventor: Robert P. Berger, 4421 Rochelle Pl., Encino, Calif. 91316

[21] Appl. No.: 686,588

[22] Filed: Dec. 26, 1984

[51] Int. Cl.[4] ............................................. A61C 19/04
[52] U.S. Cl. ..................................................... 433/72
[58] Field of Search ........................ 433/72; 33/168 R

[56] References Cited

U.S. PATENT DOCUMENTS 2,498,171  2/1950  Michler .............................. 33/168 R Primary Examiner—Robert Peshock
Attorney, Agent, or Firm—Allan M. Shapiro

[57] ABSTRACT

Dental thickness gauge is for gauging the space between a cusp and fossa during preparation for a restoration. The dental thickness gauge is a plurality of tabs in a set, with each tab being of a different thickness. The material of the tabs is tough and flexible.

20 Claims, 7 Drawing Figures

U.S. Patent  Feb. 18, 1986  4,571,181
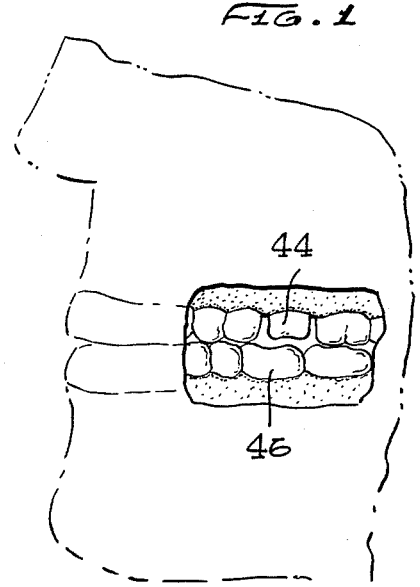
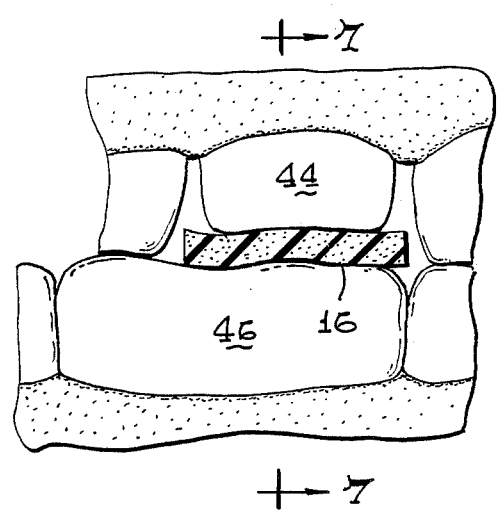
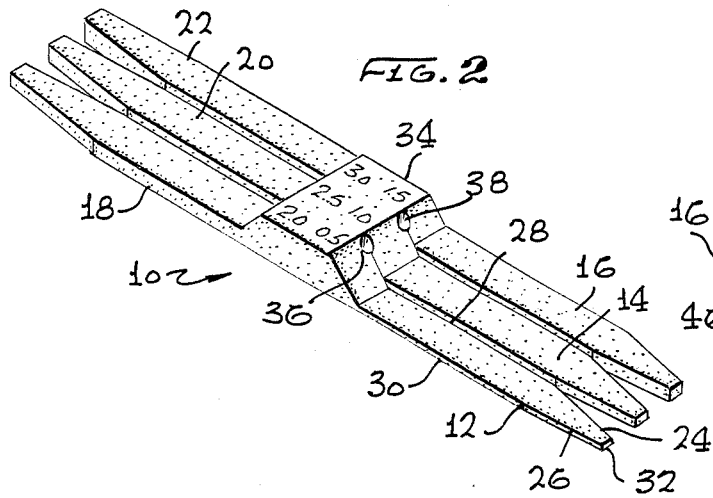
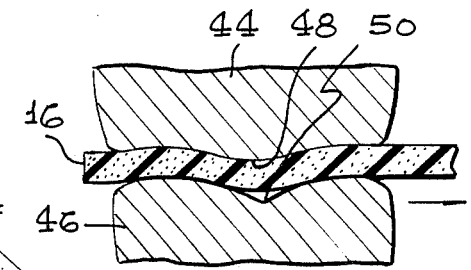
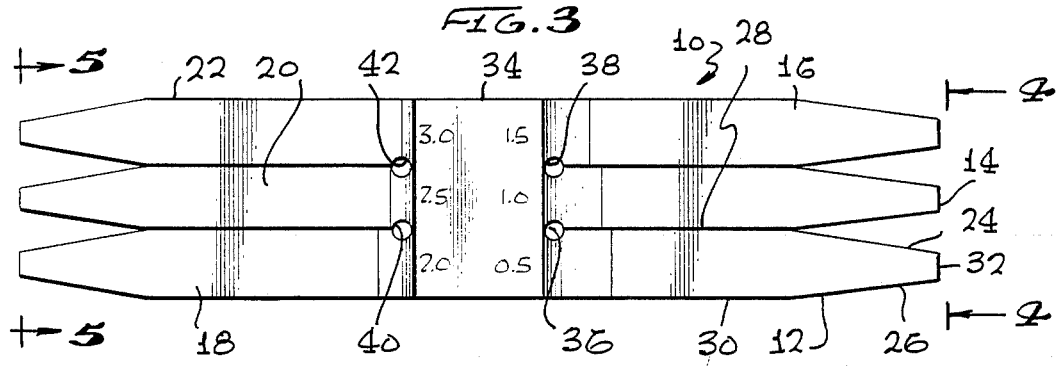
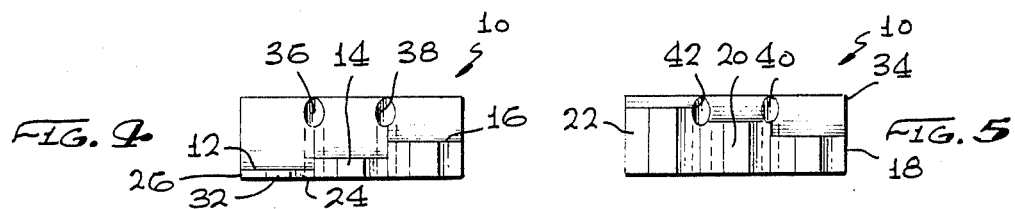

DENTAL THICKNESS GAUGE

BACKGROUND OF THE INVENTION

This invention is directed to a dental thickness gauge for gauging the correctness of space between opposing teeth during preparation for a restoration to assure that adequate space is provided for a proper restoration.

When the condition of a tooth requires a restoration, the tooth in question is prepared or cut down to both remove the portion which is decayed and to provide the space required for a proper restoration. When the restoration is to be a cast metal cap, a spacing of $\frac{1}{2}$ millimeter thickness is required to provide enough metal to provide a sufficient strength to satisfactorily resist the forces involved in chewing. Because some facing teeth intergage with cusp and fossa, it is difficult to properly estimate the spacing therebetween. At present, dentists estimate the space and a great deal of experience is required. Thus, in some cases the space is more than is necessary, which means increased preparation time and excess removal of tooth structure. When the space is less than necessary, either the restoration is too thin or the patient must be called back for further preparation work to provide the necessary space for the restoration.

Present dental practice and restoration materials require a $\frac{1}{2}$ millimeter space for a cast metal restoration. When the crown is to be a porcelain crown, a space of $1\frac{1}{2}$ millimeters is required. This is because $\frac{1}{2}$ millimeter is required for the metal substructure and a millimeter for the porcelain to be fused to the surface of the metal substructure and which creates the tooth form. The porcelain must have a thickness of 1 millimeter in order to give the restoration tooth shape and tooth color. Thus, the dental thickness gauge set requires a tab of $1\frac{1}{2}$ millimeters. In addition, when there are two such restorations facing each other, the set requires a tab of 3 millimeters. When there are two cast metal restorations opposite each other, the required space is 1 millimeter. When a cast metal restoration is to be used opposite a porcelain restoration, the required space is 2 millimeters. Thus, there is need for a dental thickness gauge which measures specific spaces in the mouth during preparation.

SUMMARY

In order to aid in the understanding of this invention, it can be stated in essentially summary form that it is directed to a dental thickness gauge which comprises a set of tabs, each of the tabs being of a thickness related to a dental preparation thickness and each of the tabs being made of a flexible, resilient and soft material so that when the preparation space is inadequate, the selected gauge is clamped between facing teeth.

It is an object and advantage of this invention to provide a dental thickness gauge which comprises a set of tabs, with each tab being of a thickness suitable for measuring the space required for a particular dental restoration, with each of the tabs being made of a flexible, soft material so that it can be clamped when tooth spacing is inadequate for the selected restoration.

It is a further object and advantage of this invention to provide a dental thickness gauge which is of easy and convenient use, and is of inexpensive manufacture so that it can be widely used both by the dentist during tooth preparation for a restoration and can be used in the dental laboratory for aiding in preparation of the required dental restoration.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a side-elevational view of a portion of the face of a human patient, with part of the cheek broken away to show a portion of the set of teeth.

FIG. 2 is an isometric view of the dental thickness gauge of this invention.

FIG. 3 is an enlarged plan view thereof.

FIG. 4 is a right-end elevational view thereof, taken on line 4—4 of FIG. 3.

FIG. 5 is a left-end elevational view thereof, taken on line 5—5 of FIG. 3.

FIG. 6 is an enlarged view of a few of the teeth shown in FIG. 1, with parts broken away, and showing the dental thickness gauge in association therewith to measure the stage of tooth preparation.

FIG. 7 is a further enlarged section taken generally along the line 7—7 of FIG. 6, with parts broken away.

DESCRIPTION OF THE PREFERRED EMBODIMENT

FIGS. 2, 3, 4 and 5 show the dental thickness gauge 10 of this invention. The gauge comprises a series of tabs, which in the preferred embodiment comprise six tabs 12, 14, 16, 18, 20 and 22. Each of the tabs has a different thickness, in the direction normal to the sheet in FIG. 3. Each of the tabs is in the form of a finger which extends in the length direction normal to the sheet in FIGS. 4 and 5. Furthermore, each of the tabs has a width direction in the upright direction of the sheet as seen in FIG. 3 and normal to the two other directions. The width and length dimensions of each of the tabs is substantially the same and, in FIG. 3, the tabs are shown as lying adjacent to each other. Throughout most of their length, the tabs are of the same width and toward the outer free ends thereof, the tabs are narrowed to a tip. Tab 12 has walls 24 and 26 which adjoin the sides 28 and 30 at their divergent end. The walls converge toward tip 32 so that at the tip the tab is more narrow than the major width of the tab between sides 28 and 30. Each of the other tabs is similarly configured.

Each of the tabs is of a different thickness. As described above, particular thickness requirements are present in preparation of teeth and restorations so they properly fit. Tabs 12, 14, 16, 18, 20 and 22 are preferably respectively of thickness 0.5 millimeter, 1.0 millimeter, 1.5 millimeter, 2.0 millimeter, 2.5 millimeter and 3.0 millimeter. The reasons for these particular thicknesses are discussed both above and below in this description. However, these thicknesses are based on present dental restoration and material technology, and changes in that technology may suggest different, or additional thickness gauges than those described herein. In addition, a different number of gauge tabs may be helpful or required with changes in materials used in dental restorations.

The gauge tabs in the set are each separately used for a separate measurement. There is no need for stacking the gauge tabs with respect to each other to obtain a total thickness. Each gauge tab is used individually. However, for the sake of being able to find the desired gauge tab, it is preferable that the gauge tabs be retained in a set. In view of the fact that the material, described below, can be injection-molded, it is convenient to mold the several gauge tabs in association with a single tab holder.

The particular thickness of each tab is defined in accordance with a particular need in dentistry to measure a particular space. The tabs of each are substantially the same width, with the distance between the sides 28 and 30 being approximately the width of a tooth space, as is seen in FIG. 6. This permits each tab to be used to test the gap spacing without interfering with adjacent teeth. The tips of the tabs are narrowed, as described above, in order to permit them to be used where the region to be tested is less than the usual full tooth width. The length of each tab is sufficient that the adjacent tabs may be bent away and the selected tab can be placed between the teeth where the preparation space is to be tested. The tab is sufficiently long that a sufficient portion extends from the mouth that the dentist can pull upon it to see if it is indented by the teeth when they are in centric relation, or unindented so that it may be easily withdrawn.

Tab holder 34 is a rectangular body of the same material as the tabs and the tabs are integrally molded therewith. The tabs are separate fingers lying adjacent to each other, and where the fingers join the tab holder body, circular cylindrical openings are provided parallel to the thickness of the tabs. Openings 36 and 38 are provided between the tabs on the right side of the body, as seen in FIG. 3, and openings 40 and 42 are provided between the tabs on the left side of that body. The openings relieve the stress raiser which would otherwise be present if the sides of the adjacent tabs lay together in a narrow slit.

The nature of the material is very important to the proper utilization of the dental thickness gauge. The material is an injection-moldable rubberlike material. It is identified as Kraton G-7705 supplied by Shell Chemical Company. The material is flexible and soft; it is injection-moldable so that parts can be made economically; it has a high thermoplastic point at 425° F. so that it can be sterilized without deformation. Preferable hardness is between a 25 and 30 Shore. With this material of this hardness, the gauge is flexible enough so that it can bend between the cusp and fossa of opposing teeth and so that it can be indented when the space between the opposing teeth is not as large as the thickness of the gauge.

FIGS. 1, 6 and 7 shown teeth in various stages of preparation. Tooth 44 is to be prepared for a restoration. It faces tooth 46. As seen in FIG. 7, tooth 44 has cusp 48 which faces fossa 50. The dentist grinds away tooth 44. He removes the decayed material and, in addition to the removal of the decay, the dentist must remove sufficient material to provide a space for the restoration. If the restoration is going to be a cast metal restoration, a ½ millimeter spacing is enough. If the restoration is going to be a metal substructure covered with fused porcelain, the spacing must be 1.5 millimeters. Assuming that it is to be a porcelain-on-metal substructure restoration, the dentist chooses tab 16 for testing the spacing. The patient opens his mouth; the dentist places the selected tab at the interengaging tooth surfacces; and the patient closes his mouth. As he closes his mouth, the tab flexes to fit the contours defined by the cusp and fossa. With the patient's jaw closed, the dentist attempts to withdraw tab 16. If there is inadequate space, the tab can be readily withdrawn because, even though it is flexed by the facing contours of the teeth, it is not indented by the teeth. However, if the space is inadequate, the tooth surfaces indent and grasp the tab and it is difficult to withdraw. The dentist can sense the inadequacy of the preparation space and cut to provide adequate space. He makes the additional cuts, places the selected tab between the tooth he has cut and the opposing tooth, and asks the patient to bite down. This position of the teeth is called the centric relation, when the teeth are in their closest position. With the jaws in centric relation, the tab follows the contours of the teeth because of the softness of the material. If the dentist pulls on the guide, in the direction of the arrow of FIG. 7, if there is inadequate spacing, he will not be able to easily pull the guide from between the teeth because the teeth indent into the tab and prevent easy withdrawal. If there is proper clearance, then the dentist will be able to easily slide the tab from between the teeth, even though it is flexed between the cusp and fossa. In this way, the dentist can assure himself that proper space is provided for a proper restoration.

In the dental laboratory, the technician uses a similar procedure with the dental thickness gauge. The laboratory is provided with reproductions of the patient's upper and lower jaws. These reproductions are placed on an articulator which holds the reproductions in position. The laboratory technician places the selected tab for the type of desired restoration between the duplication of the prepared tooth and the opposing tooth. If the gauge indicates inadequate clearance, he knows he should not begin making this restoration without indicating to the dentist that there is inadequate clearance.

The laboratory technician also uses the dental thickness gauge to help him in the fabrication of pontics. A pontic is a replacement for one or more teeth which are missing. The pontics are suspended by preparing a vital tooth on each side of the missing tooth area. A wax frame is prepared, including the abutments mounted on the adjacent vital teeth and the bridge therebetween. The structure is first built up in wax and, as it is built, the technician knows that he must have a 1 millimeter space between the metal frame and the opposing tooth so that there is proper thickness for the dental glass. Thus, when the technician is making the wax pattern, he uses the 1 millimeter gauge tab together with the wax structure on the articulator. With this relationship, he can remove wax or add wax so that the gauge shows he has the exact clearance that he needs. It is in this dental laboratory use that the 2.5 millimeter tab 20 becomes of value. When the technician is building up a pontic which requires a 1 millimeter glass space thereover, and the opposing tooth will receive a restoration of porcelain on metal, the total space will be 2.5 millimeters. Thus, after the pontic is prepared the technician can measure for adequate space for the porcelain-on-metal restoration. By use of the dental thickness gauge 10 of this invention, the proper clearance can be achieved under various circumstances.

This invention has been described in its presently contemplated best mode and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A dental thickness gauge comprising:
   a plurality of tabs, each of said tabs being of substantially uniform thickness and each of said tabs being of a different preselected thickness, each of said tabs having a length and a width suitable for placement of a selected tab between the two cusp and fossa opposing surfaces of two opposing teeth to determine the space between the teeth, each of said tabs being made of a flexible, resilient material which is three dimensional flexible so as to flex into a concave fossa under the pressure of the pointed cusp of the opposing tooth, and so that the tab will be indented in a cusp shaped three dimensional curve when the spacing between opposing teeth is less than the thickness of the tab so that ease of withdrawal of the tab indicates adequate spacing.

2. The dental thickness gauge of claim 1 wherein each said tab is made of a resilient, rubberlike material having a hardness of substantially 25 to 30 Shore.

3. The dental thickness gauge of claim 1 wherein each of said tabs is substantially rectangular in cross section.

4. The dental thickness gauge of claim 3 wherein each of said tabs is secured to a tab holder by which the tabs are retained in the gauge set.

5. The dental thickness gauge of claim 4 wherein each said tab is made of a resilient, rubberlike material having a hardness of substantially 25 to 30 Shore.

6. The dental thickness gauge of claim 4 wherein said tab holder is a sutstantially rectangular body and said tabs are integrally formed with said body.

7. The dental thickness gauge of claim 6 wherein said plurality of tabs in said body are integrally molded of thermoplastic synthetic polymer composition material.

8. The dental thickness gauge of claim 7 wherein each said tab is made of a resilient, rubberlike material having a hardness of substantially 25 to 30 Shore.

9. The dental thickness gauge of claim 7 wherein said synthetic polymer composition material has a plastic point sufficiently high so that said dental thickness gauge can be sterilized without significant deformation of said gauge.

10. The dental thickness gauge of claim 9 wherein each said tab is made of a resilient, rubberlike material having a hardness of substantially 25 to 30 Shore.

11. A dental thickness gauge comprising:
    a tab, said tab being made of a resilient, rubberlike material which can bend in three dimensions said tab being of a selected thickness for measuring the preparation space between the non-planar non-parallel cusp and fossa surfaces of opposing teeth, said tab having a width substantially equal to tooth width and a length sufficiently long so that a portion of said tab can be placed between the opposing tooth and a portion thereof extends from the mouth for grasp and withdrawal so that the resiliency of said tab permits three dimensional flexure of said tabs between the cup-shaped cusp and fossa of the opposing teeth and ease of withdrawal indicates adequacy of preparation space.

12. The dental thickness gauge of claim 11 wherein the thickness of said tab is selected from the group consisting of 0.5 millimeter, 1.0 millimeter, 1.5 millimeter, 2.0 millimeter, 2.5 millimeter and 3.0 millimeter.

13. The dental thickness gauge of claim 11 wherein said gauge is made of a thermoplastic synthetic polymer composition material having a hardness of about 25 to 30 Shore so that said tab can flex between the cusp and fossa and be indented by the opposing teeth without substantial tooth-closing force and yet said tab substantially returns to its unstressed configuration.

14. The dental thickness gauge of claim 13 wherein the thickness of said gauge is selected from the group consisting of 0.5 millimeter, 1.0 millimeter, 1.5 millimeter, 2.0 millimeter, 2.5 millimeter and 3.0 millimeter.

15. The dental thickness gauge of claim 14 wherein said thermoplastic synthetic polymer composition material does not become plastic up to at least 250° F. so that said dental thickness gauge can be sterilized without losing its configuration.

16. The method of gauging the preparation space between opposing teeth comprising the steps of selecting a tab from a set of tabs wherein each of the tabs has a known thickness;
    placing the tab between the patient's opposing teeth where the preparation space is being made and closing the patient's mouth to engage the tab between opposing teeth;
    permitting the closing of the teeth to resiliently deform the tab around the cusp and fossa of the opposing teeth; and
    manually withdrawing the tab from the opposing teeth with the patient's mouth closed and sensing whether or not the preparation space is greater and smaller than the tab thickness by the required withdrawal force.

17. The method of gauging in accordance with claim 16 wherein selecting the tab comprises selecting one tab from a group of tabs having a thickness of 0.5 millimeter, 1.0 millimeter, 1.5 millimeter, 2.0 millimeter, 2.5 millimeter and 3.0 millimeter.

18. The method of claim 16 further including the preliminary step of thermoplastically molding the tab from thermoplastic synthetic polymer composition material.

19. The method of claim 18 wherein the step of molding the tab comprises the step of molding a plurality of tabs of different thickness together on a body.

20. The method of gauging in accordance with claim 19 wherein selecting the tab comprises selecting one tab from a group of tabs having a thickness of 0.5 millimeter, 1.0 millimeter, 1.5 millimeter, 2.0 millimeter, 2.5 millimeter and 3.0 millimeter.

* * * * *